United States Patent

Grotkopp et al.

[11] 4,316,912
[45] Feb. 23, 1982

[54] COMBATING PESTS WITH 1,1-DIMETHYL-INDAN-4-yl N-ALKYL-CARBAMIC ACID ESTERS

[75] Inventors: Detlef Grotkopp, Duesseldorf; Karlfried Wedemeyer, Cologne; Wilhelm Brandes, Leichlingen; Hans Scheinpflug, Leverkusen; Peter Roessler, Bergisch-Gladbach, all of Fed. Rep. of Germany

[73] Assignee: Bayer Aktiengesellschaft, Leverkusen, Fed. Rep. of Germany

[21] Appl. No.: 122,159

[22] Filed: Feb. 19, 1980

Related U.S. Application Data

[63] Continuation of Ser. No. 936,992, Aug. 25, 1978, abandoned.

[30] Foreign Application Priority Data

Aug. 31, 1977 [DE] Fed. Rep. of Germany ....... 2739192

[51] Int. Cl.³ .................. A01N 47/10; C07C 125/067
[52] U.S. Cl. ..................................... 424/300; 560/134
[58] Field of Search ..................... 560/134; 424/300

[56] References Cited

U.S. PATENT DOCUMENTS

| | | | |
|---|---|---|---|
| 2,870,057 | 1/1959 | Hartle et al. | 560/134 |
| 3,084,096 | 4/1963 | Lambrech | 560/134 |
| 3,597,472 | 8/1971 | Heiss et al. | 560/134 |
| 3,712,915 | 1/1973 | Seyberlich et al. | 560/134 |

Primary Examiner—Natalie Trousof
Assistant Examiner—Frederick W. Pepper
Attorney, Agent, or Firm—Sprung, Felfe, Horn, Lynch & Kramer

[57] ABSTRACT

1,1-Dimethyl-indan-4-yl N-alkyl-carbamic acid esters of the formula

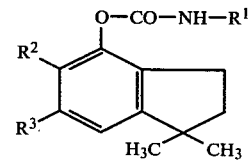

in which
  $R^1$ is alkyl, and
  $R^2$ and $R^3$ each independently is hydrogen or alkyl, which possess fungicidal and arthropod development-inhibiting properties.

5 Claims, No Drawings

COMBATING PESTS WITH 1,1-DIMETHYL-INDAN-4-yl N-ALKYL-CARBAMIC ACID ESTERS

This is a continuation, of application Ser. No. 936,992, filed Aug. 25, 1978 now abandoned.

The present invention relates to and has for its objects the provision of particular new 1,1-dimethylindan-4-yl N-alkyl-carbamic acid esters which possess pesticidal properties, active compositions in the form of mixtures of such compounds with solid and liquid dispersible carrier vehicles, and methods for producing such compounds and for using such compounds in a new way especially for combating pests, with other and further objects becoming apparent from a study of the within specification and accompanying examples.

It has already been disclosed that N-methyl-carbamic acid esters of 4-hydroxy-indans are insecticidally active (see DT-AS (German Published Specification) 1,249,261 or U.S. Pat. No. 3,597,472, and DT-OS (German Published Specification) 1,768,555 or U.S. Pat. No. 3,712,915). Furthermore, it has already been disclosed that N-trichloromethylthio-tetrahydrophthalimide exhibits powerful fungicial properties (see Science, 115, 84 (1952). This active compound, which is important in practice and is known world-wide, however, only has a protective activity.

Active compounds which inhibit the metamorphosis of arthropods have only in recent time been of interest in plant protection. In this context there may be mentioned, for example, 2,2-dimethyl-6-methoxy-benzopyran (Chem. Eng. News 54, 19-20 (1976)).

The present invention now provides, as new compounds, the indan-4-yl N-alkyl-carbamic acid esters of the general formula

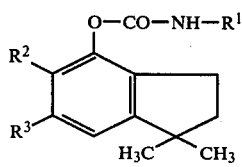

(I)

in which

R¹ represents alkyl and
R² and R³, which may be identical or different, each represent hydrogen or alkyl.

Preferably, R¹ represents alkyl with 1 to 4 carbon atoms and R² and R³ each represent hydrogen or alkyl with 1 to 4 carbon atoms.

The indan-4-yl N-alkyl-carbamates according to the invention exhibit a surprisingly great fungicidal action and are superior to the previously known N-trichloromethylthiotetrahydrophthalimide, even when used in low amounts. Furthermore, they can be used not only as protective but also as curative agents. Accordingly, the compounds according to the invention represent an enrichment of the art. For use as plant protection agents, it is of interest that the active compounds are capable of inhibiting the development of arthropods.

The invention also provides a process for the preparation of an indan-4-yl N-alkyl-carbamic acid ester of the formula (I), in which (a) a 4-hydroxy-indan of the general formula

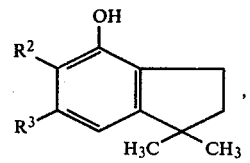

(II)

in which

R² and R³ have the above-mentioned meanings, is reacted with an alkyl isocyanate, or (b) a 4-hydroxy-indan of the formula (II) is converted, in a first step, to the corresponding chlorocarbonic acid ester by means of an excess of phosgene, and this ester is reacted, in a second step, with an alkylamine, or (c) a 4-hydroxy-indan of the formula (II) is reacted, in a first step, with an equivalent amount of phosgene to give the corresponding bis-indanyl carbonate, and this is split, in a second step, with an alkylamine.

If 4-hydroxy-1,1,5,6-tetramethyl-indan and methyl isocyanate are used as starting materials in process variant (a), the course of the reaction can be represented by the following equation:

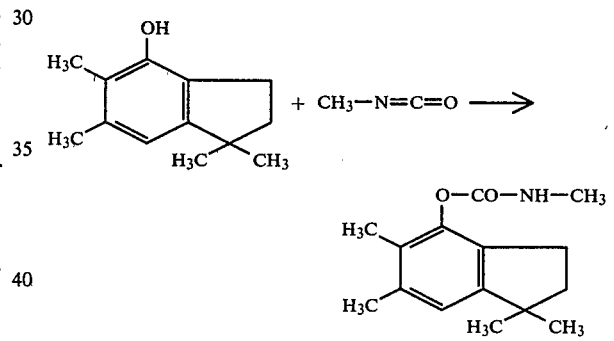

If 4-hydroxy-1,1,5,6-tetramethyl-indan, phosgene and methylamine are used as starting materials in process variant (b), the course of the reaction can be represented by the following equation:

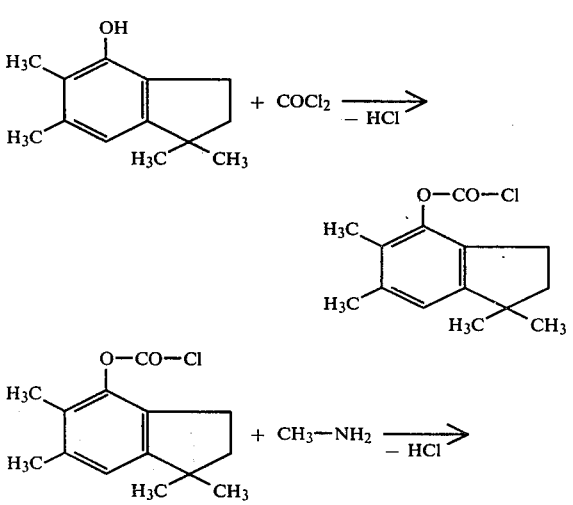

If 4-hydroxy-1,1,5,6-tetramethyl-indan, phosgene and methylamine are used as starting materials in process variant (c), the course of the reaction can be represented by the following equation:

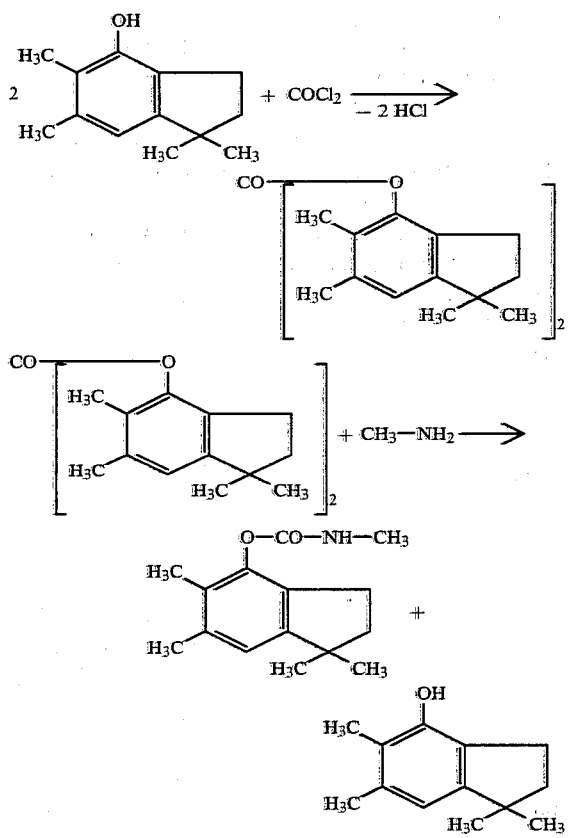

Amongst the 4-hydroxy-indans (II), 4-hydroxy-1,1,5,6-tetramethyl-indan has already been disclosed (see U.S. Pat. No. 3,057,929). The compounds are prepared by isomerizing the corresponding chromanes in the presence of Friedel-Crafts catalysts. Thus, for example, 4-hydroxy-1,1,5-trimethyl-indane is obtainable by treating 2,2,8-trimethylchromane with aluminum (III) chloride.

The chromanes used for the preparation of the 4-hydroxy-indans of the formula (II) can be obtained by reacting phenols, for example o-cresol or 2,3-dimethylphenol, with isoprene (see Houben-Weyl, Methoden der organischen Chemie (Methods of Organic Chemistry), 4th edition, volumes 6/1c, page 987–989 (1976)).

The other starting materials required for the preparation of the compounds of the formula (I), namely phosgene and alkyl isocyanate for process variant (a), or phosgene and alkylamine for process variants (b) and (c), are generally known. Examples of the alkyl isocyanates and alkylamines which should be mentioned are methyl isocyanate, ethyl isocyanate, butyl isocyanate, methylamine, ethylamine, isopropylamine, butylamine and isobutylamine.

The reaction according to process variant (a) can be carried out in an inert solvent. Suitable solvents for this purpose are, for example, hydrocarbons, such as benzine and benzene, chlorinated hydrocarbons, such as chlorobenzene, and ethers, such as dioxane; mixtures of these solvents can be used. The reaction is catalysed by adding a tertiary amine, for example triethylamine or diazobicyclooctane. The reaction temperatures can be varied within a substantial range. In general, however, the reaction will be carried out at from 0° to 150° C., preferably at from 20° to 110° C.

If process variant (b) is used, the 4-hydroxy-indan of the formula (II) is converted, in a first stage, into the chlorocarbonic acid ester by means of an excess of phosgene, advantageously in the presence of an inert solvent, such as an aromatic, optionally chlorinated, hydrocarbon, for example benzene, toluene, xylene or chlorobenzene. The resulting hydrochloric acid is bound by dropwise addition of a base, advantageously sodium hydroxide, and the pH value of the reaction solution is thus kept above 7. In general, the reaction will be carried out at a reaction temperature of from −20° to +20° C., preferably from −10° to +10° C. In the second stage, the chlorocarbonic acid ester is reacted, either after isolation or directly in the reaction solution obtained, with the equivalent amount of alkylamine. This reaction is again advantageously carried out in the presence of an inert solvent, such as an aromatic or aliphatic, optionally chlorinated, hydrocarbon, such as benzene, toluene, chlorobenzene, benzine or carbon tetrachloride, or an ether, such as dioxane. The reaction temperatures can again be varied within a certain range; in general, the reaction is carried out at from −20° to +20° C., preferably at from −10° to +10° C.

Finally, if the reaction is carried out in accordance with process variant (c), the 4-hydroxy-indan of the formula (II) is reacted, in the first stage, with an equivalent amount of phosgene to give the bis-indanyl carbonic acid ester. The reaction is advantageously carried out in an inert solvent, such as an aromatic hydrocarbon, for example benzene or toluene, while binding the hydrochloric acid formed by adding a base, preferably an alkali metal hydroxide. The pH value of the reaction solution should be about 8. The reaction temperature can vary within a substantial range, and is in general from 0° to 100° C., preferably from 20° to 60° C. The carbonate formed in the first stage is subsequently split by means of an alkylamine. This is advantageously carried out without a solvent. The reaction can, however, also be carried out in a solvent. The reaction temperature is generally from −30° to +40° C., preferably from −10° to +20° C.

The active compounds according to the invention exhibit a powerful fungitoxic action. They do not damage crop plants in the concentrations required for combating fungi. For these reasons, they are suitable for use as plant protection agents for combating fungi. Fungitoxic agents are employed in plant protection for combating Plasmodiophoromycetes, Oomycetes, Chytridiomycetes, Zygomycetes, Ascomycetes, Basidiomycetes and Deuteromycetes.

The active compounds according to the invention have a broad spectrum of action and can be used against parasitic fungi which attack above-ground parts of plants or which attack the plants through the soil, as well as against seed-borne pathogens.

They display a particularly good activity against parasitic fungi on above-ground parts of plants.

As plant protection agents, the active compounds according to the invention can be used with particularly good success for combating species of Venturia, for example for combating apple scab (*Fusioladium dendriticum*). It is to be noted that the active compounds not only have a protective, but also a curative, action.

The active compounds are well tolerated by plants, have a favorable level of toxicity to warm-blooded animals, and can be used for combating arthropod pests, especially insects and acarids, and nematode pests which are encountered in agriculture, in forestry, in the protection of stored products and of materials, and in the hygiene field. They are active against normally sensitive and resistant species and against all or some stages of development. The abovementioned pests include:

from the class of the Isopoda, for example *Oniscus anellus, Armadillidium vulgare* and *Porcellio scaber;* from the class of the Diplopoda, for example *Blaniulus guttulatus;* from the class of the Chilopoda, for example *Geophilus carpophagus* and Scutigera spec.;

from the class of the Symphyla, for example *Scutigerella immaculata;* from the order of the Thysanura, for example *Lepisma saccharina;* from the order of the Collembola, for example *Onychiurus armatus;* from the order of the Orthoptera, for example *Blatta orientalis, Periplaneta americana, Leucophaea manderae, Blattella germanica, Acheta domesticus,* Gryllotalpa spp., *Locusta migratoria migratorioides, Malanoplus differentialis* and *Schistocerca gregaria;* from the order of the Dermaptera, for example *Forficula auricularia;* from the order of the Isoptera, for example Reticulitermes spp.;

from the order of the Anoplura, for example *Phylloxera vastatrix,* Pemphigus spp., *Pediculxs humanus corporis,* Haematopinus spp. and Linognathus spp.;

from the order of the Mallophaga, for example Trichodectes spp. and Damalinea spp.;

from the order of the Thysanoptera, for example *Hercinothrips femoralis* and *Thrips tabaci;* from the order of the Heteroptera, for example Eurygaster spp., *Dysderous intermedius, Piesma quadrata, Cimex lectularius, Rhodnius prolixus* and Triatoma spp.;

from the order of the Homoptera, for example *Aleurodes brassicae, Bemisia tabaci, Trialeurodes vaporariorum, Aphis gossypii, Brevicoryne brassicae, Cryptomysus ribis, Doralis fabae, Doralis pomi, Eriosoma lanigerum, Hyalopterus arundinis, Macrosiphum avenae,* Mysus spp., *Phorodon humuli, Rhopalosiphum padi,* Empoasca spp., *Buscelis bilobatus, Nephotettix cincticeps, Lecanium corni, Saissetia oleae, Laodelphax striatellus, Nilaparvata lugens, Aonidiella aurantii, Aspidiotus Nederae, Pseudococcus* spp. and Psylla spp.;

from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Cacoecia podana, Capua reticulana, Choristoneura fumiferana, Clysia ambiguella, Homona magnanima* and *Tortrix viridana;* from the order of the Coleoptera, for example *Anobium punctatum, Rhizopertha dominica, Bruchidius obtectus, Acanthoselides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthenomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes geneus, Ptinus spp., Niptus hololeucus, Gibbium psylloides,* tribolium spp., *Tenebrio molitor,* Agriotes spp., Conoderus spp., *Melolontha melolontha, Amphimallon soistitialis* and *Costelytra zealandica;* from the order of the Hymenoptera, for example Diprion spp., Hoplocampa spp., Lasius spp., *Monomorium pharaonis* and Vespa spp.;

from the order of the Diptera, for example Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma supp., Tabanus spp., Tannia spp., *Bibio hortulanus, Oscinella frit,* Phorbia spp., *Pegomyia hyoscyami, Ceratitis capitata, Dacus oleae* and *Tipula paludosa;* from the order of the Siphonaptera, for example *Xenopsylla cheopis* and Ceratophyllus spp.;

from the class of the Arachnida, for example *Scorpio maurus* and *Latrodectus mactans;* from the order of the Acarina, for example *Acarus siro,* Argas spp., *Ornithodoros* spp., *Dermanyssus gallinae, Eriophyes ribis, Phyllocoptruta oleivora,* Boophilus spp., Rhipicophalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp..

The active compounds can be converted into the customary formulations, such as solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender organic solvents can, for example, also be used as auxiliary solvents.

As liquid solvents diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylenefatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The active compounds according to the invention can be present in the formulations as a mixture with other active compounds, such as fungicides, insecticides, acaricides, nematicides, herbicides, bird repellents, growth factors, plant nutrients and agents for improving soil structure.

The formulations in general contain from 0.1 to 95 percent by weight of active compound, preferably from 0.5 to 90 per cent.

The active compounds can be used as such, as their formulations or as the use forms prepared therefrom by further dilution, such as ready-to-use solutions, emulsions, suspensions, powders, pastes and granules. They may be used in the customary manner, for example by watering, spraying, atomizing, dusting, scattering, dry dressing, moist dressing, wet dressing, slurry dressing or encrusting.

Especially when used as leaf fungicides, the active compound concentrations in the use forms can be varied within a fairly wide range. They are, in general, from 0.1 to 0.00001 percent by weight, preferably from 0.05 to 0.0001 percent.

In the treatment of seed, amounts of active compound of 0.001 to 50 g, preferably 0.01 to 10 g, are generally employed per kilogram of seed.

As already mentioned, the compounds according to the invention inhibit the development of arthropods.

In experiments described later, the arthropod development-inhibiting action of the compounds according to the invention is demonstrated. In these experiments, the morphological changes, such as half-pupated insects, incompletely slipped larvae or caterpillars, defective wings, pupal cuticula in images and the like, were rated as malformations over the entire stated development of the test insects. The morphological malformations, together with the insects killed during the shedding sequence or the metamorphosis, were determined.

At somewhat higher concentrations, insecticidal properties are also displayed.

The present invention also provides a fungicidal or arthropod development-inhibiting composition containing as active ingredient a compound of the present invention in admixture with a solid or liquefied gaseous diluent or carrier or in admixture with a liquid diluent or carrier containing a surface active agent.

The present invention also provides a method of combating fungi or arthropods which comprises applying to the fungi or arthropods, or to a habitat thereof, a compound of the present invention alone or in the form of a composition containing as active ingredient a compound of the present invention in admixture with a diluent or carrier.

The present invention further provides crops protected from damage by fungi or arthropods by being grown in areas in which immediately prior to and/or during the time of the growing a compound of the present invention was applied alone or in admixture with a diluent or carrier.

It will be seen that the usual methods of providing a harvested crop may be improved by the present invention.

The preparation of the novel compounds is shown in the following illustrative examples:

EXAMPLE 1

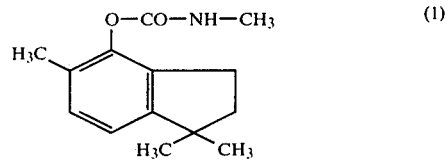

34 g (about 0.2 mol) of 4-hydroxy-1,1,5-trimethylindan were dissolved in 166 ml of ligroin at room temperature and 12 drops of triethylamine and 22 g (about 0.4 mol) of methyl isocyanate were added. After boiling for two hours under reflux, the reaction solution was allowed to cool and was then added to ice. The crystals which thereupon precipitated were filered off, washed with water, dried and recrystallized from ligroin. The yield was 38 g of 1,1,5-trimethyl-indan-4-yl N-methyl-carbamic acid ester of melting point 94.5°–95.5° C.

EXAMPLE 2

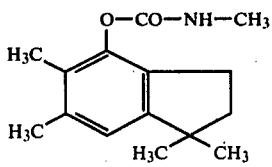

50 g (about 0.27 mol) of 4-hydroxy-1,1,5,6-tetramethylindan were dissolved in 250 ml of ligroin at room temperature and 15 drops of triethylamine and 30 gg (about 0.53 mol) of methyl isocyanate were added. After boiling for six hours under reflux, the reaction solution was allowed to cool and was then added to ice. The crystals which hereupon precipitated were filtered off, washed with water, dried and recrystallized from ligroin. The yield was 50 g of 1,1,5,6-tetramethyl-indan-4-yl N-methyl-carbamic acid ester of melting point 96.5°–97.5° C.

The following compounds of the general formula

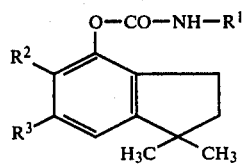

were obtained in an analogous manner to that indicated above:

| Compound No. | $R^1$ | $R^2$ | $R^3$ | Melting point (°C.) | Boiling point (°C./mmHg) |
|---|---|---|---|---|---|
| 3 | $C_2H_5$ | $CH_3$ | $CH_3$ | 58.5–60.5 | — |
| 4 | $C_2H_5$ | $CH_3$ | H | — | 132/0.07 |

The fungicidal and arthropod development-inhibiting activity of the compounds of this invention is illustrated by the following examples:

EXAMPLE 3

Fusicladium test (apple)/protective
Solvent: 4.7 parts by weight of acetone
Emulsifier: 0.3 part by weight of alkylaryl polyglycol ether
Water: 95 parts by weight The amount of active compound required for the desired concentration of the active compound in the spray liquid was mixed with the stated amount of solvent, and the concentrate was diluted with the stated amount of water which contained the stated amount of emulsifier.

Young apple seedlings in the 4–6 leaf stage were sprayed with the spray liquid until dripping wet. The plants remained in a greenhouse for 24 hours at 20 degrees (and at a relative atmospheric humidity of 70%. They were then inoculated with an aqueous conidium suspension of the apple scab causative organism (*Fusicladium dendriticum*) and incubated for 18 hours in a humidity chamber at 18°–20° and at a relative atmospheric humidity of 100%.

The plants were then brought into a greenhouse again for 14 days.

15 days after inoculation, the infection of the seedlings was determined. The compounds of Examples 1 and 2 exhibited a good action superior to a comparative formulation with a prior art compound.

EXAMPLE 4

Fusicladium test (apple scab) [Curative]
Solvent: 4.7 parts by weight of acetone
Emulsifier: 0.3 part by weight of alkylaryl polyglycol ether
Water: 95 parts by weight The amount of active compound required for the desired concentration off the active compound in the spray liquid was mixed with the stated amount of solvent, and the concentrate was diluted with the stated amount of water which contained the stated amount of emulsifier.

Young apple seedlings in the 4–6 leaf stage were inoculated with an aqueous conidium suspension of the apple scab causative organism (*Fusicladium dentriticum*) and incubated for 18 hours in a humidity chamber at 18°–20° C. and at a relative atmospheric humidity of 100%. The plants were then brought into a greenhouse and allowed to dry.

After standing for a suitable period of time, the plants were sprayed until dripping wet with the spray liquid prepared in the manner described above. The plants were then again brought into a greenhouse.

15 days after inoculation, the infection of the apple seedlings was determined. The compounds of Examples 1 and 2 exhibited a good action superior to a comparative formulation with a prior art compound.

EXAMPLE 5

Development-inhibiting action/ingestion test
Test insects *Plutella maculipennis* (caterpillars in the 4th stage of development, 20 specimens)
*Phaedon cochlearise* (larvae in the 4th stage of development, 20 specimens)
Feed plants: Cabbage plants (*Brassica oleracea*)
Solvent: 10 parts by weight of dimethylformamide
Emulsifier: 1 part by weight of polyoxyethylene sorbitan monolaurate To produce a suitable preparation of active compound, 2 parts by weight of active compound were mixed with the stated amount of solvent and of emulsifier and with sufficient water to give a 1% strength mixture, which was diluted with water to the desired concentration.

The test insects were fed with fed with leaves of the feed plants, which were provided with a uniform spray covering of the active compound mixture of the desired concentrations, so that the stated amounts of active compound in ppm (parts per million) were obtained of the leaves, until the imago developed.

As a control, leaves provided only with solvent and emulsifier of the stated concentration were used as the feed.

In this test, the compounds according to the invention disclosed in Examples 1 and 2 showed a good activity.

It will be appreciated that the instant specification and examples are set forth by way of illustration and not limitation and that various modifications and changes may be made without departing from the spirit and scope of the present invention.

What is claimed is:

1. A 1,1-dimethyl-indan-4-yl N-alkyl-carbamic acid ester selected from the group consisting of 1,1,5- trimethyl-indan-4-yl N-methyl-carbamic acid ester of the formula

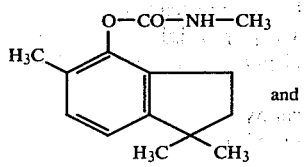

1,1,5,6-tetramethyl-indan-4-yl N-methyl-carbamic acid ester of the formula

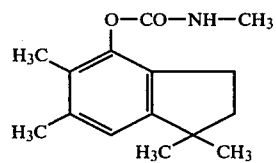

2. A compound according to claim 1, in which said compound is 1,1,5-trimethyl-indan-4-yl N-methyl-carbamic acid ester of the formula

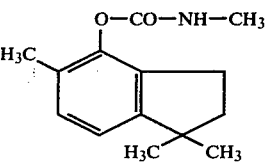

3. A compound according to claim 1, in which said compound is 1,1,5,6-tetramethyl-indan-4-yl N-methyl-carbamic acid ester of the formula

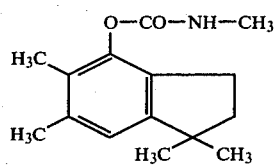

4. A fungicidal composition containing as active ingredient a fungicidally effective amount of a compound according to claim 1 in admixture with a diluent.

5. A method of combating fungi which comprises applying to the fungi, or to a habitat thereof, a fungicidally effective amount of a compound according to claim 1.

* * * * *